United States Patent [19]

Rebbe et al.

[11] 4,353,374
[45] Oct. 12, 1982

[54] BLOOD PRESSURE CUFF

[75] Inventors: Klaus Rebbe; Klaus Welimann, both of Mannheim, Fed. Rep. of Germany

[73] Assignee: Clinicon International GmbH, Mannheim, Fed. Rep. of Germany

[21] Appl. No.: 81,733

[22] Filed: Oct. 4, 1979

[30] Foreign Application Priority Data

Oct. 6, 1978 [DE] Fed. Rep. of Germany ....... 2843643

[51] Int. Cl.³ ................................................ A61B 5/02
[52] U.S. Cl. ..................................... 128/686; 128/327
[58] Field of Search ................ 128/686, 677, 678, 327

[56] References Cited

U.S. PATENT DOCUMENTS

| | | | |
|---|---|---|---|
| 2,841,149 | 7/1958 | Marsden | 128/327 |
| 3,258,009 | 6/1966 | London | 128/686 |
| 3,669,096 | 6/1972 | Hurwitz | 128/686 |
| 4,106,499 | 8/1978 | Ueda | 128/686 |

FOREIGN PATENT DOCUMENTS 67543  6/1969  German Democratic Rep. ........................ 128/686

Primary Examiner—William E. Kamm
Attorney, Agent, or Firm—Sprung, Felfe, Horn, Lynch & Kramer

[57] ABSTRACT

Blood pressure cuff having a hose-like band and buckle fixed to one end thereof through which the free end of the band is passed to form a loop, said band having a first covering made of a magnetizable sheet material which is adapted to adhere to a correspondingly magnetized oppositely applied second covering for temporary setting the loop. A self-gripping fastener can be used in place of the magnetic coverings.

8 Claims, 8 Drawing Figures

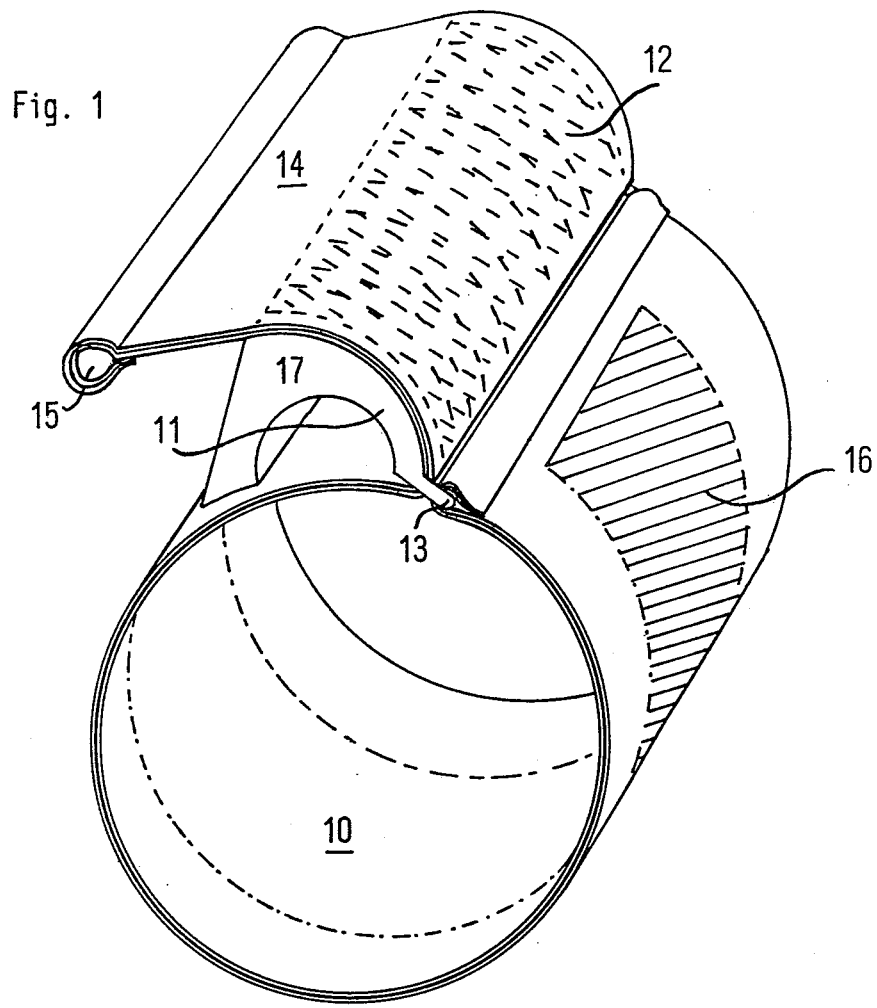

BLOOD PRESSURE CUFF

BACKGROUND

This invention relates to a cuff for use with devices which measure blood pressure (sphygmomanometers) which is basically an inflatable band which is filled with air in order to constrict the upper arm or other body member.

Known cuffs consist of a buckle to which one end of a band is permanently attached and through which the other end of the band is passed to form a loop. Such cuffs are very difficult to apply with only one hand.

The problem of one-hand application is not solved by self-gripping fasteners (e.g., Velcro) which have to be applied over a large part of the band.

SUMMARY

This invention provides a cuff which is easy to use with one hand such that the user can apply it to and release it from his own arm without assistance from another person.

The cuff of the invention is provided with a patch of magnetic material which will adhere to a correspondingly magnetized oppositely applied patch for temporarily setting or tightening the cuff.

Preferably, one crossbar of a buckle has a magnetic patch covering the entire width of the band and the cuff has a permanently magnetized counterpatch.

In another embodiment, in the case of cuffs provided with self-gripping fasteners, the self-gripping material is provided on the crossbar of the buckle over the entire width of the band.

Preferably, the crossbar of the buckle which bears the self-gripping coating is substantially larger than the other crossbar to which one end of the band is permanently attached. The crossbar bearing the magnetic or self-gripping patch is advantageously tubular in shape, with straight surfaces over the entire width of the band, so as to permit on the one hand a secure hold for the setting of the cuff and on the other hand to allow the band to pass through the buckle with as little friction as possible.

It is furthermore advantageous for the buckle to be at least half as heavy as the band, so that when the loop is opened the buckle can crop of its own weight to open the cuff.

DESCRIPTION OF THE DRAWING

Additional advantageous developments of the invention will be further explained with the aid of the embodiments represented in the drawings, where FIG. 1 is a perspective view of a closed cuff;

FIGS. 2 and 3 are cross-sections of other versions of the buckle; and

DESCRIPTION OF THE INVENTION

Figure 4A:
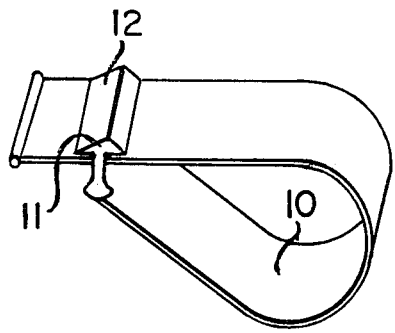
FIGS. 4a–4f illustrate various steps in the application and removal of the cuff.
Figure 4D:
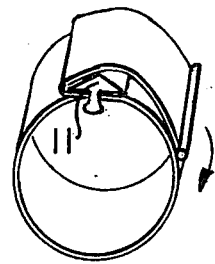

The free end of the cuff 10 represented in FIG. 1 is passed between the crossbars 13, 17 and secured by a bolster 15 against dropping out. Thus a loop is formed containing air chambers for blood pressure measurement whereby, when the loop is closed, the pressure on the encircled part of the body can be increased.

The feature of the invention lies in the relatively large crossbar 17 of the buckle in comparison to the small buckle crossbar 13. A patch 12 is applied to the crossbar 17 of the buckle 11 and adheres to the patch 16 on the cuff 10 when the two are laid one on the other.

Suitable patch materials are therefore magnetic sheet materials combined with a permanently magnetized buckle if the pattern of magnetization alternates in the direction of tension, so that the loop can be temporarily fixed in a predetermined position.

Self-gripping patches of material are commonly used which adhere to one another. For this purpose two types of material (one a plurality of hooks and the other a plurality of loops) are required. One kind of such self-gripping material is applied to the crossbar 17 in the invention. In this manner there is no transition point on the cuff 10 which weakens the cuff as such and can lead to tangling or clinging.

The manner in which the cuff represented in FIG. 1 is used is illustrated in FIGS. 4a–4f in intermediate steps. Basically, different forms of cross bar, such as those illustrated in FIGS. 2 and 3, can be used.

Figure 4B:
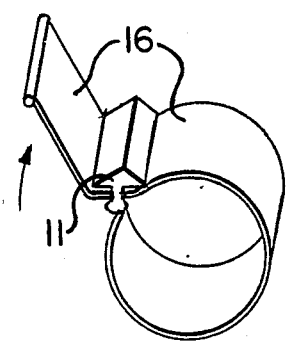
Figure 4E:
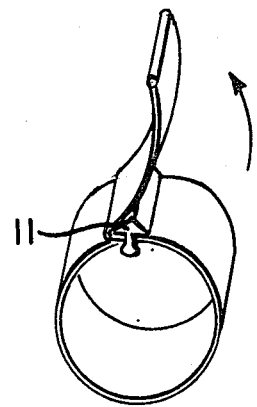
Figure 4C:
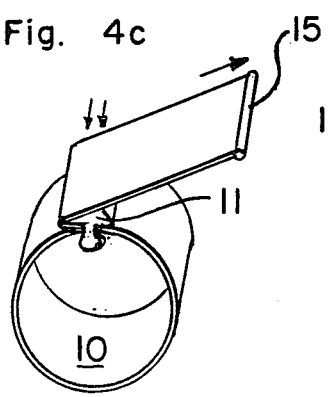

For application, the cuff is slipped over the arm in the fundamental position represented in FIG. 4a, and is drawn tight by pulling on the bolster in one direction. To tighten the loop, the direction of pull is changed (FIG. 4b). The buckle 11 slides firmly against the subject's arm. The cuff is to be fixed in this position, and for this purpose the free end is drawn by the bolster 15 over the crossbar 17 of the buckle 11. The buckle is thus fastened, without the need to drop the free end and then tighten it from underneath. The free end falls down loosely (FIG. 4d), and the cuff is ready for operation.

Figure 4F:
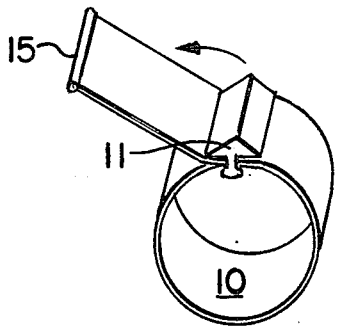

To release the cuff, the free end 15 of the cuff is lifted back over the buckle again (FIG. 4e) and the adhesion between the patches is overcome (FIG. 4f). The loop of the cuff is thus loosened again.

Since the buckle 11 is advantageously at least half as heavy as the entire cuff 10, the buckle 11 of its own weight draws the loop open again as shown in FIG. 4a. The cuff can then easily be withdrawn from the arm.

This simple mode of operation demonstrates that the new cuff can quite easily be fastened on with one hand and is therefore suitable for sphygmomanometers which can be applied without aid (i.e., without the attendance of a physician).

What is claimed is:

1. A blood-pressure cuff comprising a hose-like band; a buckle having a first crossbar and a second crossbar, one end of the band being attached to said first crossbar, and the other, free end of the band being passed between the crossbars to form a loop; and manually releasable fastening means for the temporary strapping of the loop, comprising first means disposed on the band of the cuff, and second means disposed on the second crossbar which is releasably fixable to the first means, wherein the first and second means are coverings which when placed in contact with each other form a releasable fastening.

2. The cuff according to claim 1, wherein the covering of the second means extends approximately over the entire width of the second crossbar.

3. The cuff according to claim 1 or claim 2, wherein the coverings are complementary gripping coverings.

4. The cuff according to claim 1 or claim 2, wherein the coverings are magnetic and magnetizable coverings.

5. The cuff according to claim 1, wherein the second crossbar of the buckle which bears the second means is substantially larger than the first crossbar to which the one end of the band is fixed.

6. The cuff according to claim 1, wherein the second crossbar bearing the second means is arcurate in cross-section having a diameter which is a multiple of the diameter of the first crossbar to which the one end of the band is fixed.

7. The cuff according to claim 1, wherein the second crossbar bearing the second means has straight surfaces over the entire width of the band.

8. The cuff according to claim 1, wherein the buckle is at least one-half as heavy as the band.

* * * * *

UNITED STATES PATENT AND TRADEMARK OFFICE
CERTIFICATE OF CORRECTION

PATENT NO. : 4,353,374
DATED : October 12, 1982
INVENTOR(S) : Klaus Rebbe et al

It is certified that error appears in the above—identified patent and that said Letters Patent is hereby corrected as shown below:

On the title page,

"[75] Inventors:"   Delete "Weilmann" and insert --Wellmann--

Signed and Sealed this

Twenty-eighth Day of December 1982

[SEAL]

Attest:

GERALD J. MOSSINGHOFF

Attesting Officer   Commissioner of Patents and Trademarks